United States Patent
Lee et al.

(10) Patent No.: US 10,952,650 B2
(45) Date of Patent: Mar. 23, 2021

(54) APPARATUS AND METHOD FOR ESTIMATING BLOOD SUGAR BASED ON HETEROGENEOUS SPECTRUMS

(71) Applicants: SAMSUNG ELECTRONICS CO., LTD., Suwon-si (KR); Korea University Research and Business Foundation, Seoul (KR)

(72) Inventors: Woo Chang Lee, Anyang-si (KR); Young Hoon Kim, Seoul (KR); Jin Young Park, Hwaseong-si (KR); Eui Seok Shin, Yongin-si (KR); Woo Sik Choi, Seoul (KR); Seoung Bum Kim, Seoul (KR)

(73) Assignees: SAMSUNG ELECTRONICS CO., LTD., Suwon-si (KR); Korea University Research and Business Foundation, Seoul (KR)

( * ) Notice: Subject to any disclaimer, the term of this patent is extended or adjusted under 35 U.S.C. 154(b) by 668 days.

(21) Appl. No.: 15/417,408

(22) Filed: Jan. 27, 2017

(65) Prior Publication Data

US 2018/0020958 A1    Jan. 25, 2018

(30) Foreign Application Priority Data

Jul. 19, 2016 (KR) .................... 10-2016-0091622

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/0075* (2013.01); *A61B 5/1455* (2013.01);
(Continued)

(58) Field of Classification Search
CPC . A61B 5/14532; A61B 5/1455; A61B 5/0075; A61B 5/14546; A61B 5/0059;
(Continued)

(56) References Cited

U.S. PATENT DOCUMENTS

| 6,862,534 B2 * | 3/2005 | Sterling ............ A61B 5/14532 |
| | | 702/22 |
| 7,009,180 B2 * | 3/2006 | Sterling ............ A61B 5/14532 |
| | | 250/339.09 |

(Continued)

FOREIGN PATENT DOCUMENTS

| JP | 2003-042948 A | 2/2003 |
| KR | 10-0694598 B1 | 3/2007 |

(Continued)

OTHER PUBLICATIONS

Wanjie Zhang, et al., "Discussion on the validity of NIR spectral data in non-invasive blood glucose sensing", Biomedical Optics Express, Optical Society of America, Jun. 1, 2013, vol. 4, No. 6, pp. 789-802.

(Continued)

*Primary Examiner* — May A Abouelela
(74) *Attorney, Agent, or Firm* — Sughrue Mion, PLLC

(57) ABSTRACT

An apparatus and a method for determining blood sugar based on heterogeneous spectrums are provided. The blood sugar model generation apparatus includes a data obtainer configured to obtain blood sugar profile data of a user based on a first type spectrum-blood sugar profile relationship model, a second type spectrum measurer configured to measure training second type spectrum data for the skin of the user, and a processor configured to generate an individualized blood sugar model based on the obtained blood sugar profile data and the measured training second type spectrum data.

6 Claims, 15 Drawing Sheets

(51) Int. Cl.
    *G16H 50/50*         (2018.01)
    *A61B 5/1455*      (2006.01)

(52) U.S. Cl.
    CPC .......... *A61B 5/7267* (2013.01); *A61B 5/7275* (2013.01); *A61B 5/7278* (2013.01); *G16H 50/50* (2018.01); *A61B 5/443* (2013.01); *A61B 5/4884* (2013.01); *A61B 2560/0475* (2013.01); *A61B 2562/0238* (2013.01)

(58) Field of Classification Search
    CPC ...... A61B 5/6826; G01N 33/49; G01N 21/85; G01N 2201/06113; G01N 21/35; G01N 21/359; G01N 21/65
    USPC .............. 600/300, 306, 309, 316, 319, 322; 356/39
    See application file for complete search history.

(56) References Cited

U.S. PATENT DOCUMENTS

| | | | | |
|---|---|---|---|---|
| 7,403,805 B2* | 7/2008 | Abreu | A61P 9/00 | 600/318 |
| 7,438,855 B2* | 10/2008 | Sota | A61B 5/14532 | 422/547 |
| 8,043,227 B2* | 10/2011 | Van Gogh | A61B 5/0095 | 600/306 |
| 8,121,671 B2* | 2/2012 | Hull | A61B 5/0059 | 600/316 |
| 8,335,550 B2 | 12/2012 | Segman | | |
| 8,509,867 B2* | 8/2013 | Workman | A61B 5/14532 | 436/164 |
| 2002/0016534 A1* | 2/2002 | Trepagnier | A61B 5/0059 | 600/316 |
| 2003/0031597 A1* | 2/2003 | Sota | A61B 5/14532 | 422/82.09 |
| 2003/0083558 A1* | 5/2003 | Skover | G01N 33/5091 | 600/306 |
| 2003/0176775 A1 | 9/2003 | Berman | | |
| 2003/0208169 A1* | 11/2003 | Chaiken | A61B 5/0059 | 604/310 |
| 2004/0039271 A1* | 2/2004 | Blank | A61B 5/14532 | 600/322 |
| 2004/0068163 A1* | 4/2004 | Ruchti | A61B 5/14532 | 600/316 |
| 2004/0197846 A1 | 10/2004 | Hockersmith et al. | | |
| 2004/0225206 A1* | 11/2004 | Kouchnir | A61B 5/14532 | 600/316 |
| 2006/0063988 A1* | 3/2006 | Schurman | A61B 5/0064 | 600/316 |
| 2006/0195023 A1* | 8/2006 | Acosta | A61B 5/0075 | 600/316 |
| 2006/0224057 A1* | 10/2006 | Burd | A61B 5/14532 | 600/319 |
| 2006/0276696 A1* | 12/2006 | Schurman | A61B 5/0066 | 600/316 |
| 2007/0049809 A1* | 3/2007 | Bechtel | A61B 5/14532 | 600/316 |
| 2007/0060806 A1* | 3/2007 | Hunter | A61B 5/14532 | 600/316 |
| 2007/0232873 A1* | 10/2007 | Esenaliev | A61B 5/0066 | 600/316 |
| 2009/0156915 A1* | 6/2009 | Cross | A61B 5/0066 | 600/316 |
| 2009/0247842 A1* | 10/2009 | Kallmann | A61B 5/0064 | 600/316 |
| 2009/0312615 A1* | 12/2009 | Caduff | A61B 5/0531 | 600/316 |
| 2010/0016689 A1* | 1/2010 | Kanayama | A61B 5/14532 | 600/316 |
| 2010/0298673 A1* | 11/2010 | Herrmann | A61B 5/14532 | 600/316 |
| 2011/0028806 A1* | 2/2011 | Merritt | A61B 5/0059 | 600/316 |
| 2012/0035442 A1 | 2/2012 | Barman et al. | | |
| 2012/0105470 A1 | 5/2012 | Sugiyama | | |
| 2013/0090537 A1* | 4/2013 | Schemmann | A61B 5/1455 | 600/316 |
| 2013/0094730 A1* | 4/2013 | Segman | A61B 5/0059 | 382/128 |
| 2013/0096392 A1* | 4/2013 | Adams | A61B 5/0075 | 600/301 |
| 2014/0016116 A1* | 1/2014 | Maier | G01J 3/26 | 356/39 |
| 2014/0058226 A1* | 2/2014 | Chernobrod | A61B 5/14532 | 600/316 |
| 2014/0142400 A1* | 5/2014 | Halaka | B03C 5/005 | 600/316 |
| 2014/0148658 A1* | 5/2014 | Zalevsky | A61B 5/4504 | 600/301 |
| 2014/0294675 A1 | 10/2014 | Melker et al. | | |
| 2015/0065823 A1* | 3/2015 | Liakat | A61B 5/1495 | 600/316 |
| 2015/0164393 A1* | 6/2015 | Kawamura | A61B 5/1451 | 600/316 |
| 2015/0216482 A1* | 8/2015 | Kasahara | A61B 5/1118 | 600/301 |
| 2015/0220109 A1 | 8/2015 | von Badinski et al. | | |
| 2015/0289823 A1* | 10/2015 | Rack-Gomer | G16H 20/30 | 600/365 |
| 2016/0022178 A1 | 1/2016 | Wang | | |
| 2016/0029963 A1* | 2/2016 | Hyde | A61B 5/1171 | 600/301 |
| 2016/0051180 A1* | 2/2016 | Lee | A61B 5/443 | 600/306 |
| 2016/0123869 A1* | 5/2016 | Messerschmidt | A61B 5/0261 | 356/39 |
| 2016/0192867 A1* | 7/2016 | Esenaliev | A61B 5/0095 | 600/316 |
| 2016/0258814 A1* | 9/2016 | Cho | G01J 3/42 | |
| 2017/0014056 A1* | 1/2017 | Newberry | A61B 5/14532 | |
| 2018/0020970 A1* | 1/2018 | Kim | A61B 5/0075 | 600/306 |

FOREIGN PATENT DOCUMENTS

| | | |
|---|---|---|
| KR | 10-0775669 B1 | 11/2007 |
| KR | 10-2011-0094405 A | 8/2011 |
| KR | 10-2014-0134298 A | 11/2014 |
| WO | 2013/135249 A2 | 9/2013 |

OTHER PUBLICATIONS

Bo Zeng, et al., "Noninvasive Blood Glucose Monitoring System Based on Distributed Multi-Sensors Information Fusion of Multi-Wavelength NIR", Scientific Research, Oct. 2013, Engineering, 2013, 5, pp. 553-560.

Jyoti Yadav, et al., "Near-infrared LED based Non-invasive Blood Glucose Sensor", 2014 International Conference on Signal Processing and Integrated Networks (SPIN), IEEE, pp. 591-594.

D. X. Guo, et al., "Noninvasive Blood Glucose Measurement Based on NIR Spectrums and Double ANN Analysis", Journal of Biosciences and Medicines, Scientific Research Publishing, Jun. 2015, 3, pp. 42-48.

Communication dated Oct. 17, 2017, from the European Patent Office in counterpart European Application No. 17163889.3.

Ishan Barman et al. "Development of Robust Calibration Models Using Support Vector Machines for Spectroscopic Monitoring of Blood Glucose" Analytical Chemistry, vol. 82, No. 23, Dec. 1, 2010 (pp. 9719-9726) XP055034245.

K. Danzer et al. "Near-Infrared Diffuse Reflection Spectroscopy for Non-Invasive Blood-Glucose Monitoring" Leos Newsletter, vol. 12, No. 2, Apr. 1, 1998, pp. 1-43 (44 pages total) XP002159449.

* cited by examiner

APPARATUS AND METHOD FOR ESTIMATING BLOOD SUGAR BASED ON HETEROGENEOUS SPECTRUMS

CROSS-REFERENCE TO RELATED APPLICATION

This application claims priority from Korean Patent Application No. 10-2016-0091622, filed on Jul. 19, 2016, in the Korean Intellectual Property Office, the disclosure of which is incorporated herein by reference in its entirety.

BACKGROUND

1. Field an apparatus and a method consistent with exemplary embodiments relate to a blood sugar estimation technology, and more particularly, to an apparatus and a method of estimating blood sugar using heterogeneous spectrums.

2. Description of Related Art

Nowadays, due to the living environment, adult diseases increased, causing users to be more interested in health than before. Among them, patients who suffer from adult diseases including high blood pressure, diabetes, etc. are increasing. In case of such chronic disease, while the clinic visits are necessary, it is also necessary for the patients to perform follow-up examinations of their conditions by periodically checking blood pressure and blood sugar level and take appropriate actions accordingly. For example, it is necessary for people with diabetes to monitor blood sugar about six times a day to control and maintain an appropriate blood sugar level by periodically measuring the level of sugar in blood.

Accordingly, the speed at which the use of the portable personal medical devices including blood pressure gauges, blood sugar meters, insulin pumps, etc. spreads is rapidly increasing. According to this trend, standardization of medical devices and medical services such as described above is becoming active, and personal medical devices and services utilizing them are being provided.

Currently, as one of the medical devices that measure blood sugar, there are the invasive blood sugar meters. In the method of using such an invasive blood sugar meter described above, a needle penetrates the skin and blood is directly collected to check the level of sugar in blood. However, in this method, a patient may feel pain from being pricked with a needle every time during a blood-collecting process, and there is a risk of infection of a part that is pricked with the needle. Since invasive blood sugar meters may make users uncomfortable, as described above, noninvasive blood sugar meters based on a spectroscopic analysis method capable of measuring a blood sugar level of intercellular liquid under the skin without using a needle have been developed.

However, even when using noninvasive blood sugar meters, a plurality of blood-collecting processes are still necessary to generate calibration, that is, an individualized blood sugar estimation model.

SUMMARY

This summary is provided to introduce a selection of concepts in a simplified form that are further described below in the Detailed Description of Exemplary Embodiments. This summary is not intended to identify key features or essential features of the claimed subject matter, nor is it intended to be used as an aid in determining the scope of the claimed subject matter.

The following description relates to an apparatus and a method for determining blood sugar level using heterogeneous spectrums.

In one general aspect of an exemplary embodiment, a blood sugar model generation apparatus includes a data obtainer configured to obtain blood sugar profile data of a user based on a first type spectrum-blood sugar profile relationship model, a second type spectrum measurer configured to measure training second type spectrum data for the skin of the user, and a processor configured to generate an individualized blood sugar model based on the obtained blood sugar profile data and the measured training second type spectrum data.

A first type spectrum may be a Raman spectrum, and a second type spectrum may be a near infrared (NIR) spectrum.

The first type spectrum-blood sugar profile relationship model may be generated through machine learning based on training first type spectrum data and training blood sugar profile data.

The training blood sugar profile data may be obtained by performing an oral glucose tolerance test (OGTT) on a subject whose training first type spectrum data has been measured.

The first type spectrum-blood sugar profile relationship model may be generated through machine learning with the training first type spectrum data as an input and the training blood sugar profile data as a target.

The first type spectrum-blood sugar profile relationship model may be generated through machine learning with the training first type spectrum data as an input and an area under the curve (AUC) value calculated from the training blood sugar profile data as a target.

A machine learning algorithm may be one of partial least squares regression, linear regression, neural network, decision tree, genetic algorithm, genetic programming, K-nearest neighbor, radial basis function network, random, forest, support vector machine, and deep-learning.

The second type spectrum measurer may include a light source configured to emit light to the skin of the user and a spectroscope configured to detect absorbed, scattered, or reflected light from the skin of the user and measures the training second type spectrum data based on the detected light.

The processor may generate the individualized blood sugar model through machine learning.

The processor may generate the individualized blood sugar model by calculating a blood sugar value corresponding to the measured training second type spectrum data from the obtained blood sugar profile data and through machine learning with the training second type spectrum data as an input and the calculated blood sugar value as a target.

In another general aspect of an exemplary embodiment, a blood sugar profile providing apparatus includes a memory configured to store a first type spectrum-blood sugar profile relationship model, a first type spectrum measurer configured to measure first type spectrum data for the skin of a user, and a processor configured to calculate a blood sugar profile of the user based on the first type spectrum-blood sugar profile relationship model and the measured first type spectrum data.

A first type spectrum may be a Raman spectrum.

The first type spectrum-blood sugar profile relationship model may be generated through machine learning based on training first type spectrum data and training blood sugar profile data.

The training blood sugar profile data may be obtained by performing an OGTT on a subject whose training first type spectrum data has been measured.

The first type spectrum-blood sugar profile relationship model may be generated through machine learning with the training first type spectrum data as an input and the training blood sugar profile data as a target.

The first type spectrum-blood sugar profile relationship model may be generated through machine learning with the training first type spectrum data as an input and an AUC value calculated from the training blood sugar profile data as a target.

A machine learning algorithm may be one of partial least squares regression, linear regression, neural network, decision tree, genetic algorithm, genetic programming, K-nearest neighbor, radial basis function network, random, forest, support vector machine, and deep-learning.

The first type spectrum measurer may include a light source configured to emit light to the skin of the user and a spectroscope configured to detect absorbed, scattered, or reflected light from the skin of the user and measures the first type spectrum data.

When the first type spectrum-blood sugar profile relationship model is generated through machine learning with training first type spectrum data as an input and training blood sugar profile data as a target, the processor may calculate a blood sugar profile of the user by a blood profile output by inputting the measured first type spectrum data into the first type spectrum-blood sugar profile relationship model.

When the first type spectrum-blood sugar profile relationship model is generated through machine learning with training first type spectrum data as an input and an AUC valued calculated from training blood sugar profile data as a target, the processor may calculate a blood sugar profile of the user based on an AUC value output by inputting the measured first type spectrum data into the first type spectrum-blood sugar profile relationship model.

The processor may adjust a reference blood sugar profile to allow an AUC value of the reference blood sugar profile to be the output AUC value and may calculate a blood sugar profile data of the user by the data of the adjusted reference blood sugar profile.

In still another general aspect of an exemplary embodiment, an apparatus includes a memory configured to store an individualized blood sugar model, a second type spectrum measurer configured to measure second type spectrum data for the skin of a user, and a processor configured to calculate blood sugar of the user based on the measured second type spectrum data and the individualized blood sugar model. Here, the blood sugar model is generated based on blood sugar profile data of the user based on a first type spectrum-blood sugar profile relationship model and training second type spectrum data for the skin of the user.

A first type spectrum may be a Raman spectrum, and a second type spectrum may be an NIR spectrum.

The first type spectrum-blood sugar profile relationship model may be generated through machine learning based on training first type spectrum data and training blood sugar profile data.

The training blood sugar profile data may be obtained by performing an OGTT on a subject whose training first type spectrum data has been measured.

The first type spectrum-blood sugar profile relationship model may be generated through machine learning with the training first type spectrum data as an input and the training blood sugar profile data as a target.

The first type spectrum-blood sugar profile relationship model may be generated through machine learning with the training first type spectrum data as an input and an AUC value calculated from the training blood sugar profile data as a target.

A machine learning algorithm may be one of partial least squares regression, linear regression, neural network, decision tree, genetic algorithm, genetic programming, K-nearest neighbor, radial basis function network, random, forest, support vector machine, and deep-learning.

The second type spectrum measurer may include a light source configured to emit light to the skin of the user and a spectroscope configured to detect absorbed, scattered, or reflected light from the skin of the user and measures the second type spectrum data based on the detected light.

The individualized blood sugar model may be generated through machine learning.

Other features and aspects of exemplary embodiment will become more apparent from the following detailed description of exemplary embodiment, the drawings, and the claims.

BRIEF DESCRIPTION OF THE DRAWINGS

The above and/or other aspects will be more apparent and more readily appreciated by describing from the following description of exemplary embodiments with reference to the accompanying drawings, in which.

Figure 1:
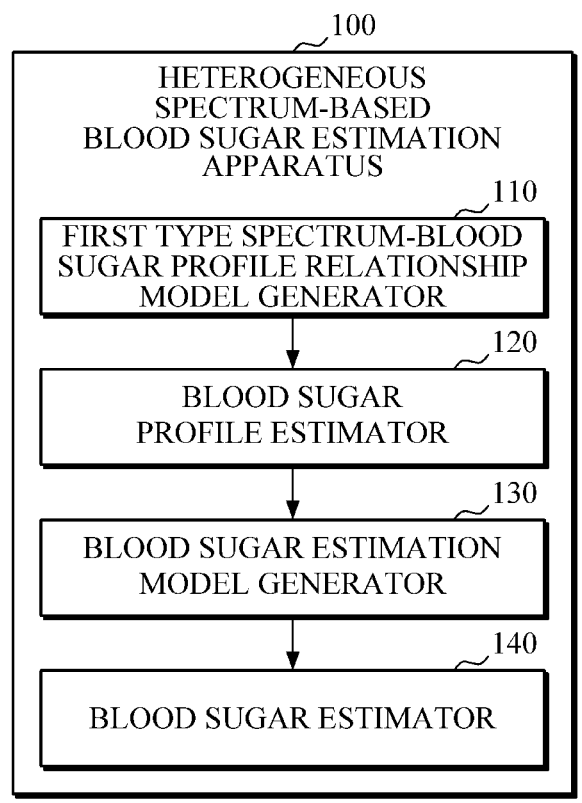
FIG. 1 is a block diagram illustrating a heterogeneous spectrum-based blood sugar estimation apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION OF EXEMPLARY EMBODIMENTS

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 is a block diagram illustrating a heterogeneous spectrum-based blood sugar estimation apparatus according to an exemplary embodiment.

Referring to FIG. 1, a heterogeneous spectrum-based blood sugar estimation apparatus 100 may include a first type spectrum-blood sugar profile relationship model generator 110, a blood sugar profile estimator 120, a blood sugar estimation model generator 130, and a blood sugar estimator 140.

The first type spectrum-blood sugar profile relationship model generator 110 may generate a model which defines a relationship between a first type spectrum and a blood sugar profile (hereinafter, a first type spectrum-blood sugar profile relationship model). Here, the first type spectrum may be a Raman spectrum for the skin and the blood sugar profile may be a trend of blood sugar in time.

According to an exemplary embodiment, the first type spectrum-blood sugar profile relationship model generator 110 may generate the first type spectrum-blood sugar profile relationship model through machine learning based on training first type spectrum data and training blood sugar profile data for skin of a subject. Here, the training blood sugar profile data may be data obtained by performing an oral glucose tolerance test (OGTT) on the subject whose first type spectrum data has been measured. Also, a machine learning algorithm may include partial least squares regression, linear regression, neural network, decision tree, genetic algorithm, genetic programming, K-nearest neighbor, radial basis function network, random, forest, support vector machine, deep-learning, etc. However, the learning algorithm is provided by way of an example and is not limited thereto.

The blood sugar profile estimator 120 may estimate blood sugar profile data of a user.

According to an exemplary embodiment, the blood sugar profile estimator 120 may estimate blood sugar profile data using a first type spectrum-blood sugar profile relationship model. For example, the blood sugar profile estimator 120 may obtain first type spectrum data for the skin of the user and may estimate blood sugar profile data of the user by inputting the obtained first type spectrum data into the first type spectrum-blood sugar profile relationship model.

The blood sugar estimation model generator 130 may generate an individualized blood sugar estimation model.

According to an exemplary embodiment, the blood sugar estimation model generator 130 may generate the individualized blood sugar estimation model through machine learning based on training second type spectrum data for the skin of the user and the blood sugar profile data of the user estimated by the blood sugar profile estimator 120. Here, a second type spectrum may be a near-infrared (NIR) spectrum.

For example, the blood sugar estimation model generator 130 may generate the individualized blood sugar estimation model through machine learning with the training second type spectrum data for the skin of the user as an input and a blood sugar value corresponding to the training second type spectrum data as a target. Here, the blood sugar value corresponding to the training second type spectrum data may be calculated from the estimated blood sugar profile data of the user.

The blood sugar estimator 140 may estimate blood sugar of the user.

According to an exemplary embodiment, the blood sugar estimator 140 may estimate the blood sugar of the user using the individualized blood sugar estimation model. For example, the blood sugar estimator 140 may obtain the second type spectrum data for the skin of the user and may estimate the blood sugar of the user by inputting the obtained second type spectrum into the blood sugar estimation model.

Meanwhile, the heterogeneous spectrum-based blood sugar estimation apparatus 100 may be embodied as a single software module or manufactured as a single hardware chip to be installed in an electronic apparatus. Otherwise, each of the components that form the heterogeneous spectrum-based blood sugar estimation apparatus 100 such as the first type spectrum-blood sugar profile relationship model generator 110, the blood sugar profile estimator 120, the blood sugar estimation model generator 130, and the blood sugar estimator 140 may be embodied as a separate software module or a separate hardware chip to be installed in a separate electronic apparatus. Here, the electronic apparatus may include a fixed terminal and a mobile terminal. The fixed terminal may include a digital television (TV), a desktop computer, etc. The mobile terminal may include a cellular phone, a smart phone, a tablet personal computer (PC), a notebook PC, personal digital assistants (PDA), a portable multimedia player (PMP), a navigation device, an MP3 player, a digital camera, a wearable device, etc. However, the electronic device is not limited to the above examples and may include various devices.

Figure 2:
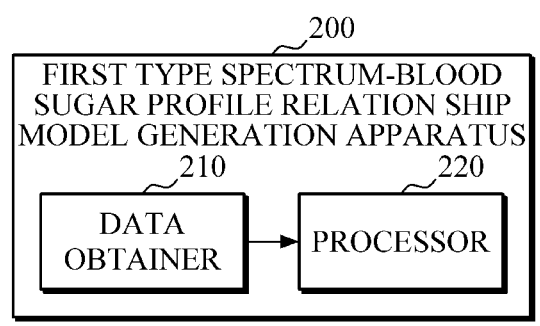
FIG. 2 is a block diagram illustrating a first type spectrum-blood sugar profile relationship model generation apparatus according to an exemplary embodiment.

FIG. 2 is a block diagram illustrating a first type spectrum-blood sugar profile relationship model generation apparatus according to an exemplary embodiment. A first type spectrum-blood sugar profile relationship model generation apparatus 200 may be an example of the first type spectrum-blood sugar profile relationship model generator 110 of FIG. 1.

Referring to FIG. 2, the first type spectrum-blood sugar profile relationship model generation apparatus 200 may include a data obtainer 210 and a processor 220.

The data obtainer 210 may obtain training first type spectrum data and training blood sugar profile data. Here, a first type spectrum may be a Raman spectrum.

According to an exemplary embodiment, the data obtainer 210 may obtain the training first type spectrum data and the training blood sugar profile data from a certain database or an external apparatus. Here, the training blood sugar profile data may be data obtained by performing an OGTT on a subject whose first type spectrum data has been measured.

The processor 220 may generate the first type spectrum-blood sugar profile relationship model through machine learning based on the training first type spectrum data and the training blood sugar profile data which are obtained. Here, a machine learning algorithm may include partial least squares regression, linear regression, neural network, decision tree, genetic algorithm, genetic programming, K-nearest neighbor, radial basis function network, random, forest, support vector machine, deep-learning, etc. but is not limited thereto.

According to an exemplary embodiment, the processor 220 may generate the first type spectrum-blood sugar profile relationship model through machine learning with the obtained training first type spectrum data as an input and training blood sugar profile data as a target.

According to another exemplary embodiment, the processor 220 may generate the first type spectrum-blood sugar profile relationship model by calculating an area under the curve (AUC) value of a training blood sugar profile from the training blood sugar profile data and through machine learning with the training first type spectrum data as an input and the calculated AUC value as a target.

Figure 3:
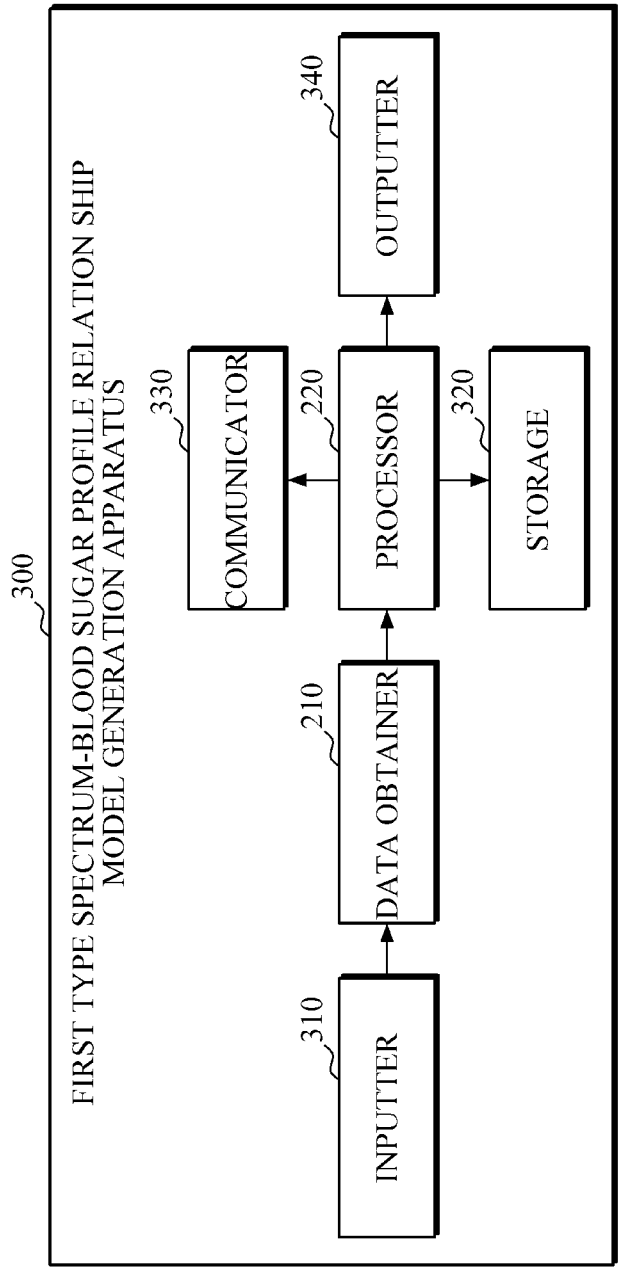
FIG. 3 is a block diagram illustrating another example of a first type spectrum-blood sugar profile relationship model generation apparatus according to an exemplary embodiment.

FIG. 3 is a block diagram illustrating another example of a first type spectrum-blood sugar profile relationship model generation apparatus according to an exemplary embodiment.

Referring to FIG. 3, compared with the first type spectrum-blood sugar profile relationship model generation apparatus 200 of FIG. 2, a first type spectrum-blood sugar profile relationship model generation apparatus 300 may selectively further include an inputter 310, a storage or a memory 320, a communicator 330, and an outputter 340.

The inputter or an input interface 310 may receive various operation signals from a user. According to an exemplary embodiment, the inputter 310 may include a key pad, a dome switch, a touch pad (static pressure/static electricity), a jog wheel, a jog switch, a hardware (H/W) button, etc. Particularly, when a touch pad and a display together form a layer structure, it may be called a touch screen.

The storage 320 may store programs or commands for operations of the first type spectrum-blood sugar profile relationship model generation apparatus 300 and may store data which are input or output. Also, the storage 320 may store a generated first type spectrum-blood sugar profile relationship model.

The storage 320 may include a flash memory type memory, a hard disk type memory, a multimedia card micro type memory, a card type memory such as a secure digital (SD) memory, an extreme digital (XD) memory, etc., a random access memory (RAM), a static random access memory (SRAM), a read only memory (ROM), an electrically erasable programmable read only memory (EEPROM), a programmable read only memory (PROM), a magnetic memory, a magnetic disk, an optical disk, etc. Also, the first type spectrum-blood sugar profile relationship model generation apparatus 300 may operate an external storage medium such as a web storage which performs a storage function of the storage 320 on the Internet.

The communicator 330 may perform communication with an external apparatus. For example, the communicator 330 may transmit data input through the inputter 310, the first type spectrum-blood sugar profile relationship model generated by the processor 220, etc. to the external apparatus or may receive data for generating the first type spectrum-blood sugar profile relationship model from the external apparatus.

Here, the external apparatus may be a medical apparatus which uses the generated first type spectrum-blood sugar profile relationship model, a printer for outputting a result, or a display apparatus which displays data related to the generated first type spectrum-blood sugar profile relationship model. In addition, the external apparatus may be a digital TV, a desktop computer, a cellular phone, a smart phone, a tablet PC, a notebook PC, PDA, a PMP, a navigation device, an MP3 player, a digital camera, a wearable device, etc. but is not limited thereto.

The outputter 340 may output data related to generating the first type spectrum-blood sugar profile relationship model and data related to the generated first type spectrum-blood sugar profile relationship model. According to an exemplary embodiment, the outputter 340 may output the data related to generating the first type spectrum-blood sugar profile relationship model and the data related to the generated first type spectrum-blood sugar profile relationship model using at least one of an acoustic method, a visual method, and a tactile method. For example, the outputter 340 may output the data related to generating the first type spectrum-blood sugar profile relationship model and the data related to the generated first type spectrum-blood sugar profile relationship model using a voice, a text, vibrations, etc. For this, the outputter 340 may include a display, a speaker, a vibrator, etc.

Figure 4:
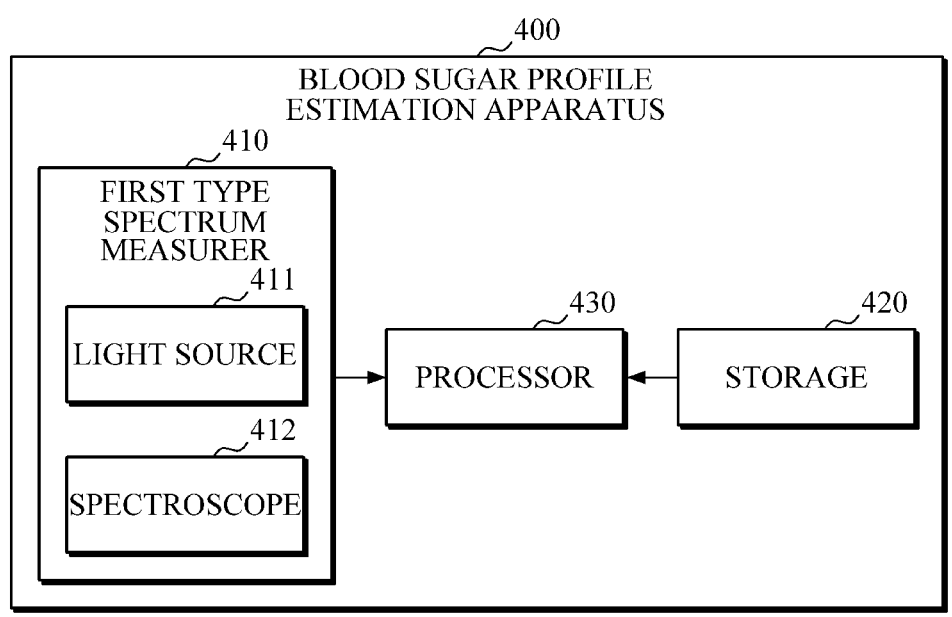
FIG. 4 is a block diagram illustrating a blood sugar profile estimation apparatus according to an exemplary embodiment.

FIG. 4 is a block diagram illustrating a blood sugar profile estimation apparatus according to an exemplary embodiment. A blood sugar profile estimation apparatus 400 may be an example of the blood sugar profile estimator 120 of FIG. 1.

Referring to FIG. 4, the blood sugar profile estimation apparatus 400 may include a first type spectrum measurer 410, a storage 420, and a processor 430.

The first type spectrum measurer 410 may measure first type spectrum data, for example, Raman spectrum data for the skin of the user. For this, the first type spectrum measurer 410 may include a light source 411 which emits light to the skin of the user and a spectroscope 412 which detects absorbed, scattered, or reflected light from the skin of the user and measures the first type spectrum data. Here, the light source 411 may include a light emitting diode (LED), a laser diode, etc. The spectroscope 412 may include a photo diode, a photo transistor (PTr), a charge-coupled device (CCD), etc.

The storage 420 may store a first type spectrum-blood sugar profile relationship model. Here, the first type spectrum-blood sugar profile relationship model may be generated through machine learning with training first type spectrum data as an input and training blood sugar profile data as a target or with training first type spectrum data as an input and an AUC value of a training blood sugar profile calculated from the training blood sugar profile data as a target.

Also, the storage 420 may store programs or commands for operating the blood sugar profile estimation apparatus 400 and may store data which are input or output.

The storage 420 may include a flash memory type memory, a hard disk type memory, a multimedia card micro type memory, a card type memory such as an SD memory, an XD memory, etc., an RAM, an SRAM, an ROM, an EEPROM, a PROM, a magnetic memory, a magnetic disk, an optical disk, etc. Also, the blood sugar profile estimation apparatus 400 may operate an external storage medium such as a web storage which performs a storage function of the storage 420 on the Internet.

The processor 430 may estimate blood sugar profile data of the user based on the measured first type spectrum data and the stored first type spectrum-blood sugar profile relationship model.

According to an exemplary embodiment, when the first type spectrum-blood sugar profile relationship model is generated through machine learning with the training first type spectrum data as the input and the training blood sugar profile data as the target, an output of the first type spectrum-blood sugar profile relationship model is provided as the blood sugar profile data. In this case, the processor 430 may estimate the blood sugar profile data output by inputting the measured first type spectrum data into the first type spectrum-blood sugar profile relationship model as the blood sugar profile data of the user.

According to another exemplary embodiment, when the first type spectrum-blood sugar profile relationship model may be generated through machine learning with the training first type spectrum data as the input and the AUC value of the training blood sugar profile calculated from the training blood sugar profile data as the target, an output of the first type spectrum-blood sugar profile relationship model is provided in the form of AUC, that is, the AUC value of the blood sugar profile of the user to be estimated. In this case, the processor 430 may estimate the blood sugar profile data of the user based on the AUC value output by inputting the measured first type spectrum data into the first type spectrum-blood sugar profile relationship model. For example, the processor 430 may adjust a reference blood sugar profile to allow an AUC value of the reference blood sugar profile to be the output AUC value, for example, adjustment of the height of a graph, and may estimate the adjusted reference blood sugar profile as the blood sugar profile of the user. Here, the reference blood sugar profile may be experimentally derived as a blood sugar profile capable of expressing blood sugar profiles of a plurality of subjects.

Figure 5:
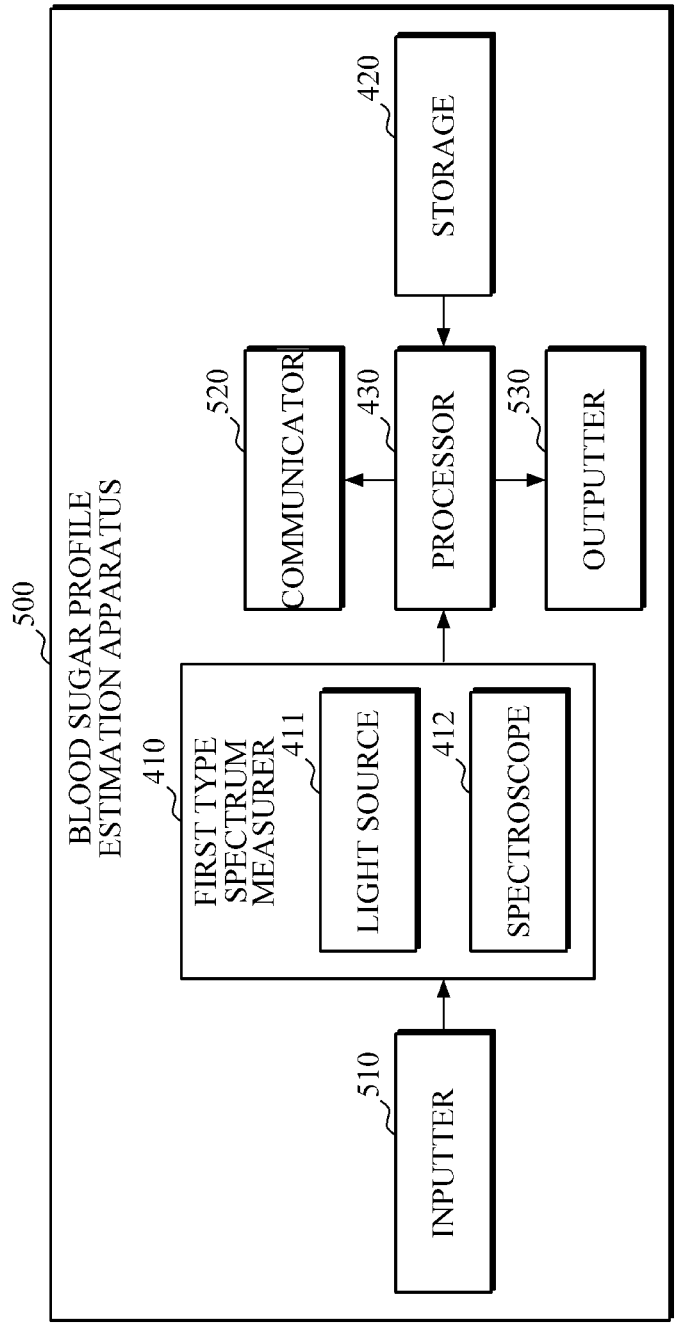
FIG. 5 is a block diagram illustrating another example of a blood sugar profile estimation apparatus according to an exemplary embodiment.

FIG. 5 is a block diagram illustrating another example of a blood sugar profile estimation apparatus according to an exemplary embodiment.

Referring to FIG. 5, compared with the blood sugar profile estimation apparatus 400 of FIG. 4, a blood sugar profile estimation apparatus 500 may further include an inputter 510, a communicator 520, and an outputter 530 selectively.

The inputter or an input interface 510 may receive various operation signals from a user. According to an exemplary embodiment, the inputter 510 may include a key pad, a dome switch, a touch pad (static pressure/static electricity), a jog wheel, a jog switch, an hardware button, etc. Particularly, when a touch pad and a display together form a layer structure, it may be called a touch screen.

The communicator 520 may perform communication with an external apparatus. For example, the communicator 520 may transmit data input through the inputter 510, blood sugar profile data of the user estimated by the processor 430, etc. to the external apparatus or may receive data for estimating the blood sugar profile data of the user from the external apparatus.

Here, the external apparatus may be a medical apparatus which uses the estimated blood sugar profile data, a printer for outputting results, or a display apparatus which displays the estimated blood sugar profile data. In addition, the external apparatus may be a digital TV, a desktop computer, a cellular phone, a smart phone, a tablet PC, a notebook PC, PDA, a PMP, a navigation device, an MP3 player, a digital camera, a wearable device, etc. but is not limited thereto.

The outputter 530 may output data related to estimation of the blood sugar profile data of the user and estimation result data. According to an exemplary embodiment, the outputter 530 may output the data related to estimation of the blood sugar profile of the user and the estimation result data using at least one of an acoustic method, a visual method, and a tactile method. For example, the outputter 530 may output the data related to estimation of the blood sugar profile data of the user and the estimation result data using a voice, a text, vibrations, etc. For this, the outputter 530 may include a display, a speaker, a vibrator, etc.

Figure 6:
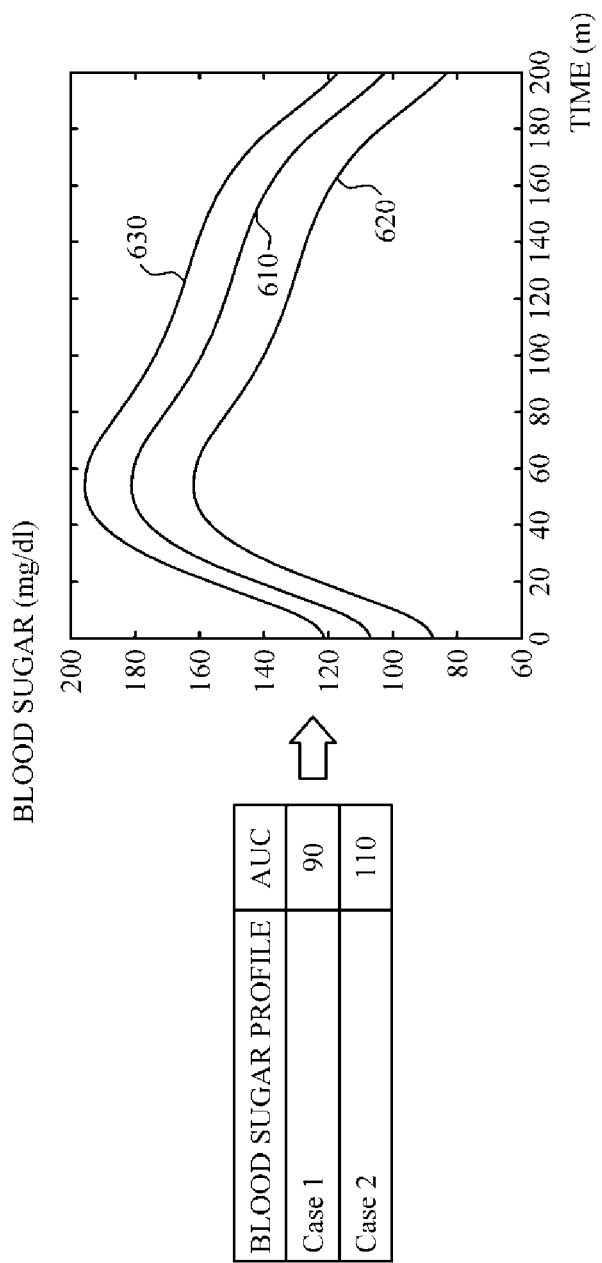
FIG. 6 is a view illustrating a method of estimating blood sugar profile data according to an exemplary embodiment.

FIG. 6 is a view illustrating a method of estimating blood sugar profile data according to an exemplary embodiment.

As described above, when a first type spectrum-blood sugar profile relationship model may be generated through machine learning with training first type spectrum data as an input and an AUC value of a training blood sugar profile calculated from training blood sugar profile data as a target, an output of the first type spectrum-blood sugar profile relationship model is provided in the form of AUC; that is, an AUC value of a blood sugar profile of a user to be estimated. In this case, the blood sugar profile estimation apparatus 400 may adjust a reference blood sugar profile to allow an AUC value of the reference blood sugar profile to be an AUC value which is output and may estimate data of the adjusted reference blood sugar profile as blood sugar profile data of the user. Here, the adjustment of the reference blood sugar profile may be performed by adjusting the height of a graph while maintaining a graph shape of the reference blood sugar profile.

In the example of FIG. 6, as a result of inputting measured first type spectrum data of the user into the first type spectrum-blood sugar profile relationship model, Case 1 indicates that the output of the first type spectrum-blood sugar profile relationship model is AUC=90, and Case 2 indicates that the output of the first type spectrum-blood sugar profile relationship model is AUC=110.

In Case 1, since the output AUC value of the first type spectrum-blood sugar profile relationship model is 90, the blood sugar profile estimation apparatus 400 adjusts a reference blood sugar profile 610 to allow an AUC value of the reference blood sugar profile 610 to be 90 and estimates data of an adjusted reference blood sugar profile 620 as the blood sugar profile data of the user.

In Case 2, since the output AUC value of the first type spectrum-blood sugar profile relationship model is 110, the blood sugar profile estimation apparatus 400 adjusts the reference blood sugar profile 610 to allow the AUC value of the reference blood sugar profile 610 to be 110 and estimates data of the adjusted reference blood sugar profile as the blood sugar profile data of the user.

Figure 7:
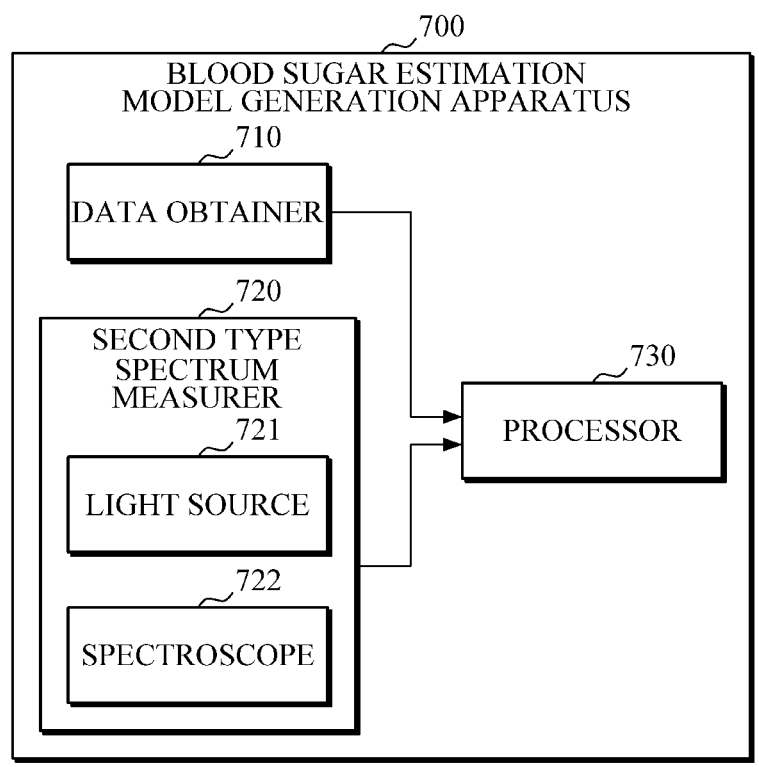
FIG. 7 is a block diagram illustrating a blood sugar estimation model generation apparatus according to an exemplary embodiment.

FIG. 7 is a block diagram illustrating a blood sugar estimation model generation apparatus according to an exemplary embodiment. A blood sugar estimation model generation apparatus 700 may be an example of the blood sugar estimation model generator 130 of FIG. 1.

Referring to FIG. 7, the blood sugar estimation model generation apparatus 700 may include a data obtainer 710, a second type spectrum measurer 720, and a processor 730.

The data obtainer 710 may obtain blood sugar profile data of a user. Here, the blood sugar profile data of the user is estimated based on a first type spectrum-blood sugar profile relationship model and first type spectrum data for the skin of the user and may be obtained from a certain database or an external apparatus. Here, a first type spectrum may be a Raman spectrum.

Meanwhile, the first type spectrum-blood sugar profile relationship model may be generated through machine learning with training first type spectrum data as an input and training blood sugar profile data as a target or with training first type spectrum data as an input and an AUC value calculated from the training blood sugar profile data as a target. The training blood sugar profile data may be obtained by performing an OGTT on a subject whose training first type spectrum data has been measured.

The second type spectrum measurer 720 may measure training second type spectrum data for the skin of the user. Here, a second type spectrum may be an NIR spectrum. For this, the second type spectrum measurer 720 may include a light source 721 which emits light to the skin of the user and a spectroscope 722 which detects absorbed, scattered, or reflected light from the skin of the user and measures second type spectrum data. Here, the light source 721 may include an LED, a laser diode, etc. The spectroscope 722 may include a photo diode, a PTr, a CCD, etc.

The processor 730 may generate an individualized blood sugar estimation model based on the obtained blood sugar profile data of the user and the measured training second type spectrum data.

According to an exemplary embodiment, the processor 730 may generate the individualized blood sugar estimation model by calculating a blood sugar value corresponding to the training second type spectrum data from the blood sugar profile data of the user and through machine learning with the training second type spectrum as an input and the calculated blood sugar value as a target. For example, as described above, since the blood sugar profile data indicates a trend of blood sugar according to time, the processor 730 may calculate a blood sugar value corresponding to a time of measuring the training second type spectrum data from the blood sugar profile data of the user.

Meanwhile, as described above, a machine learning algorithm may include partial least squares regression, linear regression, neural network, decision tree, genetic algorithm, genetic programming, K-nearest neighbor, radial basis function network, random, forest, support vector machine, deep-learning, etc. but is not limited thereto.

Figure 8:
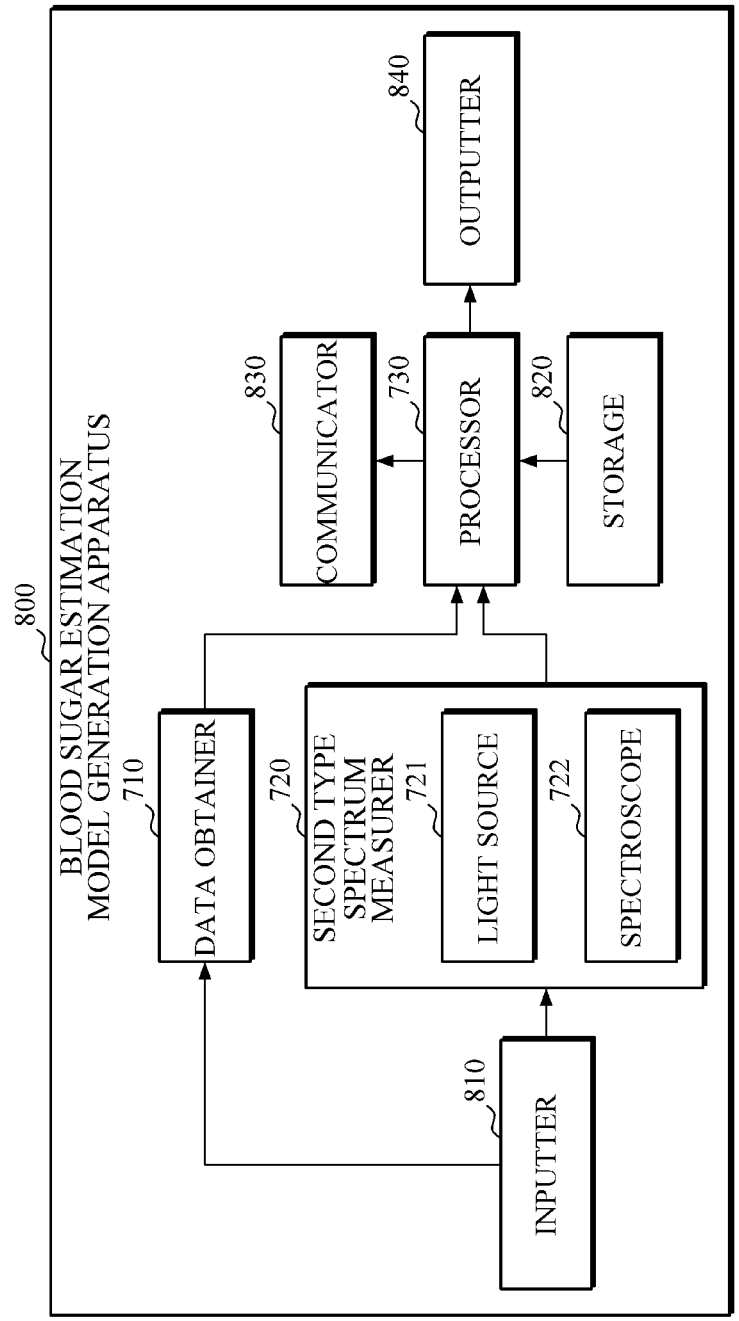
FIG. 8 is a block diagram illustrating another example of a blood sugar estimation model generation apparatus according to an exemplary embodiment.

FIG. 8 is a block diagram illustrating another example of a blood sugar estimation model generation apparatus according to an exemplary embodiment.

Referring to FIG. 8, compared with the blood sugar estimation model generation apparatus 700 of FIG. 7, a blood sugar estimation model generation apparatus 800 may further include an inputter 810, a storage 820, a communicator 830, and an outputter 840 selectively.

The inputter 810 may receive various operation signals from a user. According to an exemplary embodiment, the inputter 810 may include a key pad, a dome switch, a touch pad (static pressure/static electricity), a jog wheel, a jog switch, a hardware button, etc. Particularly, when a touch pad and a display together form a layer structure, it may be called a touch screen.

The storage 820 may store programs or commands for operating the blood sugar estimation model generation apparatus 800 and may store data which are input or output. Also, the storage 820 may store a generated individualized blood sugar estimation model.

The storage 820 may include a flash memory type memory, a hard disk type memory, a multimedia card micro type memory, a card type memory such as an SD memory, an XD memory, etc., an RAM, an SRAM, an ROM, an EEPROM, a PROM, a magnetic memory, a magnetic disk, an optical disk, etc. Also, the blood sugar estimation model generation apparatus 800 may operate an external storage medium such as a web storage which performs a storage function of the storage 820 on the Internet.

The communicator 830 may perform communication with an external apparatus. For example, the communicator 830 may transmit data input through the inputter 810, an individualized blood sugar estimation model generated by the processor 730, etc. to the external apparatus or may receive data for generating the individualized blood sugar estimation model from the external apparatus.

Here, the external apparatus may be a medical apparatus which uses the individualized blood sugar estimation mode, a printer for outputting results, or a display apparatus which displays the generated individualized blood sugar estimation model. In addition, the external apparatus may be a digital TV, a desktop computer, a cellular phone, a smart phone, a tablet PC, a notebook PC, PDA, a PMP, a navigation device, an MP3 player, a digital camera, a wearable device, etc. but is not limited thereto.

The outputter 840 may output data related to generation of the individualized blood sugar estimation model and data related to the generated individualized blood sugar estimation model. According to an exemplary embodiment, the outputter 840 may output the data related to generation of the individualized blood sugar estimation model and the data related to the generated individualized blood sugar estimation model using at least one of an acoustic method, a visual method, and a tactile method. For example, the outputter 840 may output the data related to generation of the individualized blood sugar estimation model and data related to the generated individualized blood sugar estimation model using a voice, a text, vibrations, etc. For this, the outputter 840 may include a display, a speaker, a vibrator, etc.

Figure 9:
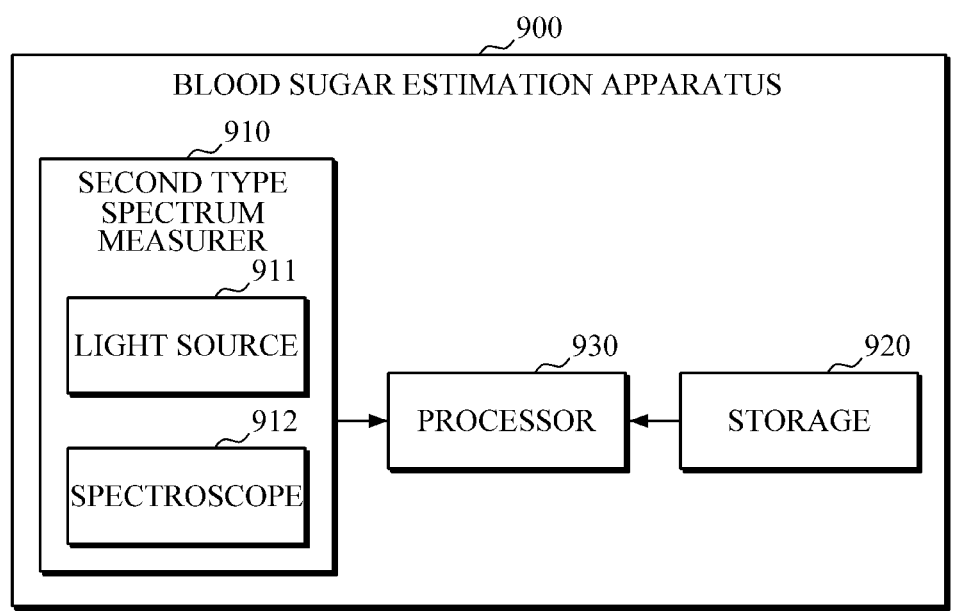
FIG. 9 is a block diagram illustrating a blood sugar estimation apparatus according to an exemplary embodiment.

FIG. 9 is a block diagram illustrating a blood sugar estimation apparatus according to an exemplary embodiment. A blood sugar estimation apparatus 900 may be an example of the blood sugar estimator 140 of FIG. 1.

Referring to FIG. 9, the blood sugar estimation apparatus 900 may include a second type spectrum measurer 910, a storage 920, and a processor 930.

The second type spectrum measurer 910 may measure second type spectrum data, for example, NIR spectrum data for the skin of the user. For this, the second type spectrum measurer 910 may include a light source 911 which emits light to the skin of the user and a spectroscope 912 which detects absorbed, scattered, or reflected light from the skin of the user and measures the second type spectrum data. Here, the light source 911 may include an LED, a laser diode, etc. The spectroscope 912 may include a photo diode, a PTr, a CCD, etc.

The storage 920 may store an individualized blood sugar estimation model. Here, the individualized blood sugar estimation model may be generated based on blood sugar profile data of the user estimated by a first type spectrum-blood sugar profile relationship model and first type spectrum data for the skin of the user and training second type spectrum data. For example, the individualized blood sugar estimation model may be generated by calculating a blood sugar value corresponding to the training second type spectrum data from the estimated blood sugar profile data of the user and through machine learning with the training second type spectrum as an input and the calculated blood sugar value as a target.

Meanwhile, the first type spectrum-blood sugar profile relationship model may be generated through machine learning with training first type spectrum data as an input and training blood sugar profile data as a target or with training first type spectrum data as an input and an AUC value of a training blood sugar profile calculated from the training blood sugar profile data as a target.

Also, the storage 920 may store programs or commands for operating the blood sugar estimation apparatus 900 and may store data which are input or output.

The storage 920 may include a flash memory type memory, a hard disk type memory, a multimedia card micro type memory, a card type memory such as an SD memory, an XD memory, etc., an RAM, an SRAM, an ROM, an EEPROM, a PROM, a magnetic memory, a magnetic disk, an optical disk, etc. Also, the blood sugar estimation apparatus 900 may operate an external storage medium such as a web storage which performs a storage function of the storage 920 on the Internet.

The processor 930 may estimate blood sugar of the user based on the measured second type spectrum data and the stored individualized blood sugar estimation model.

Figure 10:
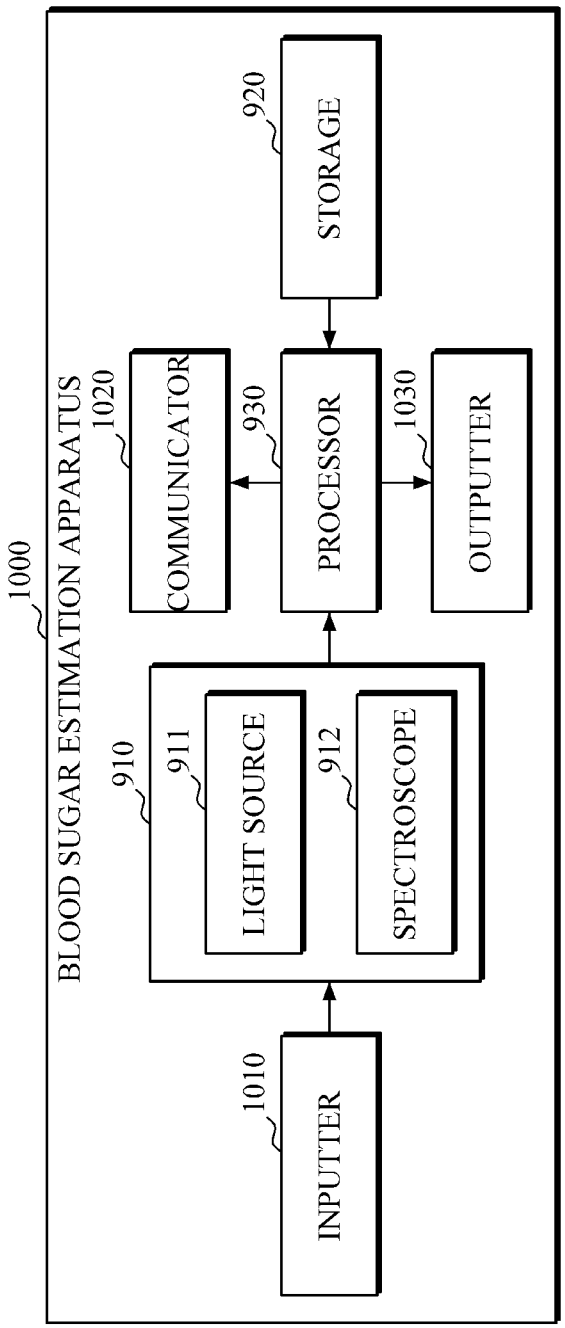
FIG. 10 is a block diagram illustrating another example of a blood sugar estimation apparatus according to an exemplary embodiment.

FIG. 10 is a block diagram illustrating another example of a blood sugar estimation apparatus according to an exemplary embodiment.

Referring to FIG. 10, compared with the blood sugar estimation apparatus 900, a blood sugar estimation apparatus 1000 may selectively further include an inputter 1010, a communicator 1020, and an outputter 1030.

The inputter 1010 may receive various operation signals from a user. According to an exemplary embodiment, the inputter 1010 may include a key pad, a dome switch, a touch pad (static pressure/static electricity), a jog wheel, a jog switch, a hardware button, etc. Particularly, when a touch pad and a display together form a layer structure, it may be called a touch screen.

The communicator 1020 may perform communication with an external apparatus. For example, the communicator 1020 may transmit data input through the inputter 1010, blood sugar of the user estimated by the processor 930, etc. to the external apparatus or may receive data for estimating the blood sugar of the user from the external apparatus.

Here, the external apparatus may be a medical apparatus which uses estimated blood sugar data of the user, a printer for outputting results, or a display apparatus which displays the estimated blood sugar data. In addition, the external apparatus may be a digital TV, a desktop computer, a cellular phone, a smart phone, a tablet PC, a notebook PC, PDA, a PMP, a navigation device, an MP3 player, a digital camera, a wearable device, etc. but is not limited thereto.

The outputter 1030 may output data related to estimation of the blood sugar of the user and estimation result data. According to an exemplary embodiment, the outputter 1030 may output the data related to estimation of the blood sugar of the user and the estimation result data using at least one of an acoustic method, a visual method, and a tactile method. For example, the outputter 1030 may output the data related to estimation of the blood sugar of the user and the estimation result data using a voice, a text, vibrations, etc. For this, the outputter 1030 may include a display, a speaker, a vibrator, etc. By way of an example, based on the estimation of the blood sugar level of the user, an alarm may be output when the estimation of the blood sugar level of the user exceeds a predetermined threshold. In an exemplary embodiment, the apparatus which detects the blood sugar level 1000 may be a specialized medical device which measures light reflected from the skin of the user to detect the user's sugar blood level, as described above by way of an example.

Figure 11:
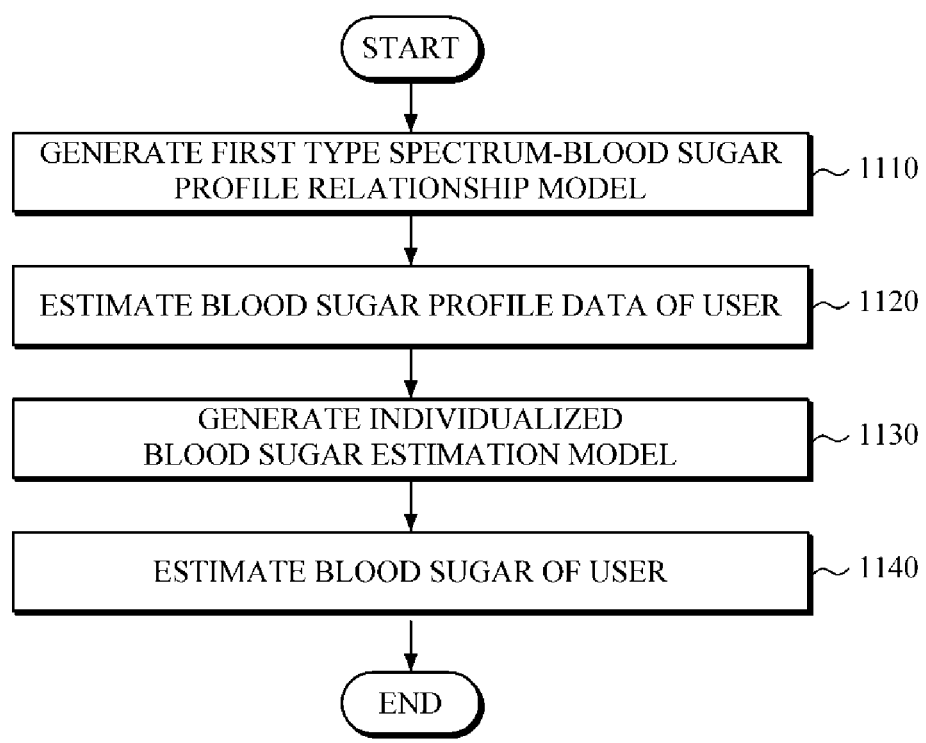
FIG. 11 is a flowchart illustrating a method of estimating blood sugar based on a heterogeneous spectrum according to an exemplary embodiment.

FIG. 11 is a flowchart illustrating a method of estimating blood sugar based on a heterogeneous spectrum according to an exemplary embodiment.

Referring to FIGS. 1 and 11, the heterogeneous spectrum-based blood sugar estimation apparatus 100 may generate a first type spectrum-blood sugar profile relationship model through machine learning based on training first type spectrum data and training blood sugar profile data (in operation 1110). Here, a first type spectrum may be a Raman spectrum for the skin and a blood sugar profile may be a trend of blood sugar level at predetermined times or a trend of blood sugar over time.

The heterogeneous spectrum-based blood sugar estimation apparatus 100 may estimate blood sugar profile data of a user using the generated first type spectrum-blood sugar profile relationship model (in operation 1120). For example, the heterogeneous spectrum-based blood sugar estimation apparatus 100 may obtain first type spectrum data for the skin of the user and may estimate blood sugar profile data of the user by inputting the obtained first type spectrum data into the first type spectrum-blood sugar profile relationship model.

The heterogeneous spectrum-based blood sugar estimation apparatus 100 may generate an individualized blood sugar estimation model through machine learning based on training second type spectrum data for the skin of the user and the estimated blood sugar profile data of the user (in operation 1130). Here, a second type spectrum may be an NIR spectrum.

For example, the heterogeneous spectrum-based blood sugar estimation apparatus 100 may generate the individualized blood sugar estimation model through machine learning with the training second type spectrum data for the skin of the user as an input and a blood sugar value corresponding to the training second type spectrum data as a target. Here, the blood sugar value corresponding to the training second type spectrum data may be calculated from the estimated blood sugar profile data of the user.

The heterogeneous spectrum-based blood sugar estimation apparatus 100 may estimate blood sugar of the user using the individualized blood sugar estimation model (in operation 1140). For example, the heterogeneous spectrum-based blood sugar estimation apparatus 100 may obtain the second type spectrum data for the skin of the user and may estimate the blood sugar of the user by inputting the obtained second type spectrum into the blood sugar estimation model.

Figure 12:
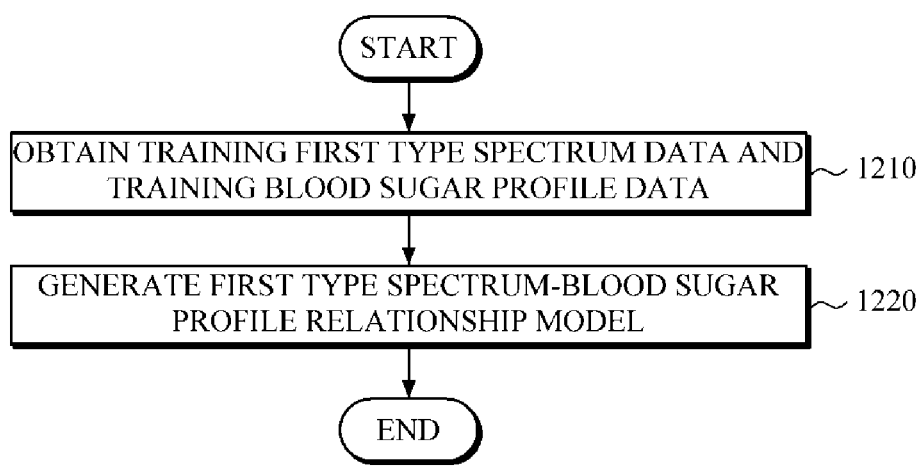
FIG. 12 is a flowchart illustrating a method of generating a first type spectrum-blood sugar profile relationship model according to an exemplary embodiment.

FIG. 12 is a flowchart illustrating a method of generating a first type spectrum-based blood sugar profile relationship model according to an exemplary embodiment.

Referring to FIGS. 2 and 12, according to an exemplary embodiment, the first type spectrum-blood sugar profile relationship model generation apparatus 200 may obtain training first type spectrum data and training blood sugar profile data (in operation 1210). Here, a first type spectrum may be a Raman spectrum.

For example, the first type spectrum-blood sugar profile relationship model generation apparatus 200 may obtain training first type spectrum data and the training blood sugar profile data from a certain database or an external apparatus. Here, the training blood sugar profile data may be data obtained by performing an OGTT on a subject whose first type spectrum data has been measured.

The first type spectrum-blood sugar profile relationship model generation apparatus 200 may generate a first type spectrum-blood sugar profile relationship model through machine learning based on the obtained training first type spectrum data and training blood sugar profile data (in operation 1220). For example, the first type spectrum-blood sugar profile relationship model generation apparatus 200 may generate the first type spectrum-blood sugar profile relationship model through machine learning with the training first type spectrum data as an input and the training blood sugar profile data as a target or with the training first type spectrum data as an input and an AUC value calculated from the training blood sugar profile data as a target.

Figure 13:
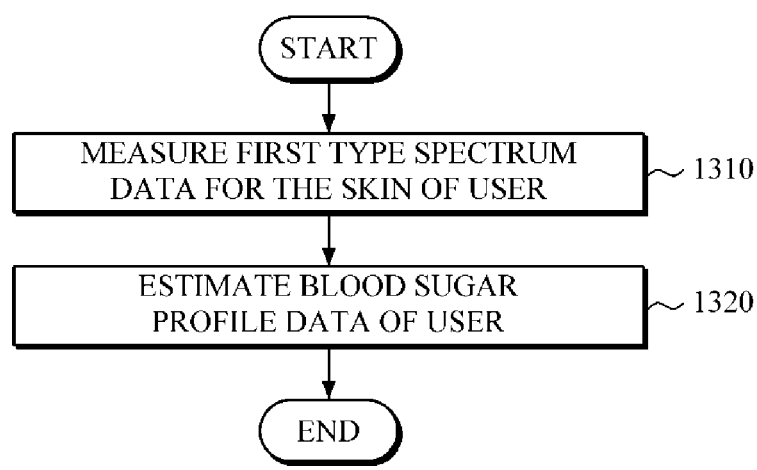
FIG. 13 is a flowchart illustrating a method of estimating a blood sugar profile according to an exemplary embodiment.

FIG. 13 is a flowchart illustrating a method of estimating a blood sugar profile according to an exemplary embodiment.

Referring to FIGS. 4 and 13, the blood sugar profile estimation apparatus 400 may estimate first type spectrum data for the skin of a user (in operation 1310). Here, a first type spectrum may be a Raman spectrum.

The blood sugar profile estimation apparatus 400 may estimate blood sugar profile data of the user based on the measured first type spectrum data and a stored first type spectrum-blood sugar profile relationship model (in operation 1320). Here, the first type spectrum-blood sugar profile relationship model may be generated through machine learning with training first type spectrum data as an input and training blood sugar profile data as a target or with training first type spectrum data as an input and an AUC value of a training blood sugar profile calculated from the training blood sugar profile data as a target.

According to an exemplary embodiment, when the first type spectrum-blood sugar profile relationship model may be generated through machine learning with the training first type spectrum data as the input and the training blood sugar profile data as the target, the blood sugar profile estimation apparatus 400 may estimate blood sugar profile data output by inputting the first type spectrum data into the first type spectrum-blood sugar profile relationship model as the blood sugar profile data of the user.

According to another exemplary embodiment, when the first type spectrum-blood sugar profile relationship model is generated through machine learning with the training first type spectrum data as the input and the AUC value of the blood sugar profile calculated from the training blood sugar profile data as the target, the blood sugar profile estimation apparatus 400 may estimate the blood sugar profile data of the user based on the AUC value output by inputting the measured first type spectrum data into the first type spectrum-blood sugar profile relationship model.

Figure 14:
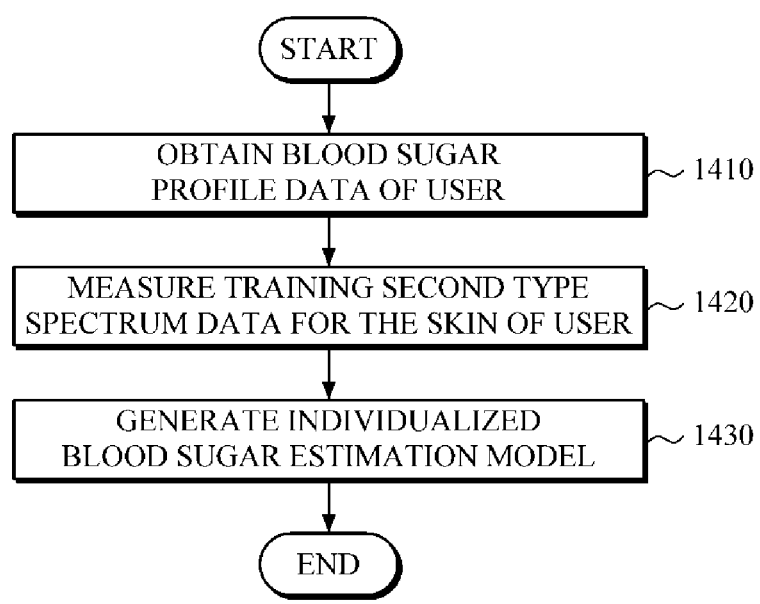
FIG. 14 is a flowchart illustrating a method of generating a blood sugar estimation model according to an exemplary embodiment.

FIG. 14 is a flowchart illustrating a method of generating a blood sugar estimation model according to an exemplary embodiment.

Referring to FIGS. 7 and 14, the blood sugar estimation model generation apparatus 700 may obtain blood sugar profile data of a user (in operation 1410). Here, the blood sugar profile data of the user is estimated based on a first type spectrum-blood sugar profile relationship model and first type spectrum data for the skin of the user and may be obtained from a certain database or an external apparatus. Here, a first type spectrum may be a Raman spectrum.

Meanwhile, the first type spectrum-blood sugar profile relationship model may be generated through machine learning with training first type spectrum data as an input and training blood sugar profile data as a target or with training first type spectrum data as an input and an AUC value calculated from the training blood sugar profile data as a target. The training blood sugar profile data may be obtained by performing an OGTT on a subject whose training first type spectrum data has been measured.

The blood sugar estimation model generation apparatus 700 may measure training second type spectrum data for the skin of the user (in operation 1420). Here, a second type spectrum may be an NIR spectrum.

The blood sugar estimation model generation apparatus 700 may generate an individualized blood sugar estimation model based on the obtained blood sugar profile data of the user and the measured training second type spectrum data (in operation 1430). For example, the blood sugar estimation model generation apparatus 700 may generate the individualized blood sugar estimation model by calculating a blood sugar value corresponding to the training second type spectrum data from the blood sugar profile data of the user and through machine learning with the training second type spectrum as an input and the calculated blood sugar value as a target.

Figure 15:
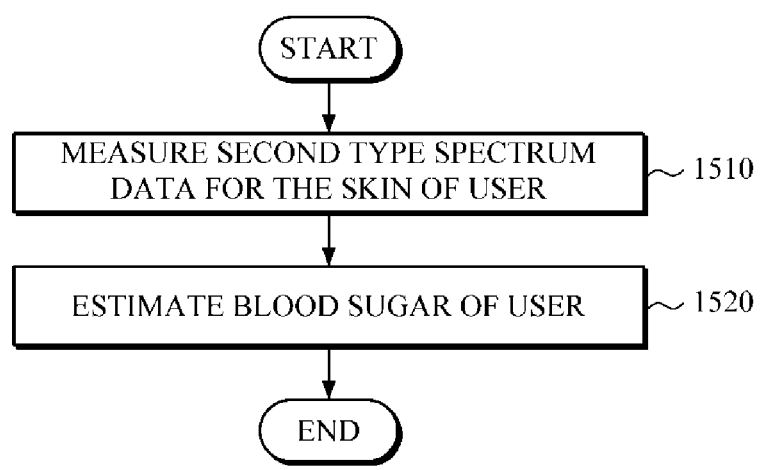
FIG. 15 is a flowchart illustrating a method of estimating blood sugar according to an exemplary embodiment.

FIG. 15 is a flowchart illustrating a method of estimating blood sugar according to an exemplary embodiment.

Referring to FIGS. 9 and 15, the blood sugar estimation apparatus 900 may estimate second type spectrum data for the skin of a user (in operation 1510). Here, a second type spectrum may be an NIR spectrum.

The blood sugar estimation apparatus 900 may estimate blood sugar of the user based on the measured second type spectrum data and a stored individualized blood sugar estimation model (in operation 1520). Here, the individualized blood sugar estimation model may be generated based on blood sugar profile data of the user estimated by a first type spectrum-blood sugar profile relationship model and first type spectrum data for the skin of the user and training second type spectrum data. For example, the individualized blood sugar estimation model may be generated by calculating a blood sugar value corresponding to the training second type spectrum data from the estimated blood sugar profile data of the user and through machine learning with the training second type spectrum as an input and the calculated blood sugar value as a target.

Meanwhile, the first type spectrum-blood sugar profile relationship model may be generated through machine learning with training first type spectrum data as an input and training blood sugar profile data as a target or with training first type spectrum data as an input and an AUC value of a training blood sugar profile calculated from the training blood sugar profile data as a target.

Exemplary embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in different order and/or if components in a described system, architecture, device, or circuit are combined in a different manner and/or replaced or supplemented by other components or their equivalents. Accordingly, other implementations are within the scope of the following claims.

What is claimed is:

1. A blood sugar model generation apparatus comprising:
a storage that stores computer code; and
a processor that accesses and executes the computer code to:
generate a first type spectrum-blood sugar profile relationship model by training the first type spectrum-blood sugar profile relationship model using first type spectrum data and blood sugar profile data on a plurality of subjects whose first type spectrum data have been measured;
calculate blood sugar profile data of a user based on the first type spectrum-blood sugar profile relationship model and obtained first type spectrum data for skin of the user;
generate an individualized blood sugar model by training the individualized blood sugar model using second type spectrum data for the skin of the user and blood sugar values calculated from the blood sugar profile data of the user and corresponding to the second type spectrum data; and
estimate a blood sugar value of the user using the individualized blood sugar model and an obtained second type spectrum data for the skin of the user, wherein the first type spectrum is a different type of spectrum from the second type spectrum.

2. The blood sugar model generation apparatus of claim 1, wherein the first type spectrum is a Raman spectrum, and the second type spectrum is a near infrared (NIR) spectrum.

3. The blood sugar model generation apparatus of claim 1, wherein the blood sugar profile data is obtained by performing an oral glucose tolerance test (OGTT) on the subjects whose first type spectrum data has been measured.

4. The blood sugar model generation apparatus of claim 1, wherein the first type spectrum-blood sugar profile relationship model is generated by training the first type spectrum-blood sugar profile relationship model using the first type spectrum data and an area under a curve (AUC) value calculated from blood sugar profile data.

5. The blood sugar model generation apparatus of claim 1, wherein the training comprises a machine learning algorithm selected from among partial least squares regression, linear regression, neural network, decision tree, genetic algorithm, genetic programming, K-nearest neighbor, radial basis function network, random, forest, support vector machine, and deep-learning.

6. The blood sugar model generation apparatus of claim 1, further comprising:
a light source configured to emit light to the skin of the user; and
a spectroscope configured to detect absorbed, scattered, or reflected light from the skin of the user,
wherein the second type spectrum data is measured based on the detected light.

* * * * *